United States Patent
MacDowell et al.

(10) Patent No.: US 9,057,681 B2
(45) Date of Patent: Jun. 16, 2015

(54) HIGH-TEMPERATURE STRAIN CELL FOR TOMOGRAPHIC IMAGING

(71) Applicants: Alastair A. MacDowell, Berkeley, CA (US); James Nasiatka, San Francisco, CA (US); Abdel Haboub, Richmond, CA (US); Robert O. Ritchie, Berkeley, CA (US); Hrishikesh A. Bale, Walnut Creek, CA (US)

(72) Inventors: Alastair A. MacDowell, Berkeley, CA (US); James Nasiatka, San Francisco, CA (US); Abdel Haboub, Richmond, CA (US); Robert O. Ritchie, Berkeley, CA (US); Hrishikesh A. Bale, Walnut Creek, CA (US)

(73) Assignee: The Regents of the University of California, Oakland, CA (US)

( * ) Notice: Subject to any disclaimer, the term of this patent is extended or adjusted under 35 U.S.C. 154(b) by 36 days.

(21) Appl. No.: 14/081,948

(22) Filed: Nov. 15, 2013

(65) Prior Publication Data
US 2014/0161223 A1    Jun. 12, 2014

Related U.S. Application Data

(60) Provisional application No. 61/734,737, filed on Dec. 7, 2012.

(51) Int. Cl.
*G01N 23/00* (2006.01)
*H01J 35/14* (2006.01)
*G01N 23/04* (2006.01)

(52) U.S. Cl.
CPC ...... *G01N 23/046* (2013.01); *G01N 2223/3106* (2013.01); *G01N 2223/607* (2013.01); *G01N 2223/419* (2013.01)

(58) Field of Classification Search
CPC ....... A61L 2/082; G01N 23/046; H01J 35/00; H01J 35/14
USPC .......................... 378/119, 122, 20, 208, 6, 64
See application file for complete search history.

(56) References Cited

U.S. PATENT DOCUMENTS

| | | | | |
|---|---|---|---|---|
| 5,323,442 | A  * | 6/1994 | Golovanivsky et al. | 378/119 |
| 6,262,818 | B1 * | 7/2001 | Cuche et al. | 359/9 |
| 2012/0307962 | A1 * | 12/2012 | Cho | 378/6 |
| 2013/0078624 | A1 * | 3/2013 | Holmes et al. | 435/6.11 |
| 2014/0161223 | A1 * | 6/2014 | MacDowell et al. | 378/20 |

OTHER PUBLICATIONS

Bale et al., Nature Materials 12, 40-46 (2013).
Stock, S. R. Recent advances in X-ray microtomography applied to materials. Int. Mater. Rev. 53, 129-181 (2008).

(Continued)

*Primary Examiner* — David A Vanore
(74) *Attorney, Agent, or Firm* — Lawrence Berkeley National Laboratory

(57) ABSTRACT

This disclosure provides systems, methods, and apparatus related to the high temperature mechanical testing of materials. In one aspect, a method includes providing an apparatus. The apparatus may include a chamber. The chamber may comprise a top portion and a bottom portion, with the top portion and the bottom portion each joined to a window material. A first cooled fixture and a second cooled fixture may be mounted to the chamber and configured to hold the sample in the chamber. A plurality of heating lamps may be mounted to the chamber and positioned to heat the sample. The sample may be placed in the first and the second cooled fixtures. The sample may be heated to a specific temperature using the heating lamps. Radiation may be directed though the window material, the radiation thereafter interacting with the sample and exiting the chamber through the window material.

20 Claims, 4 Drawing Sheets

(56) References Cited

OTHER PUBLICATIONS

Sakdinawat, A. & Attwood, D. Nanoscale X-ray imaging. Nature Photon. 4, 840-48 (2010).
Terzi, S. et al. In situ X-ray tomography observation of inhomogeneous deformation in semi-solid aluminium alloys. Scr. Mater. 61, 449-452 (2009).

Kinney, J. H. & Nichols, M. C. X-ray tomographic microscopy (XTM) using synchrotron radiation. Annu. Rev. Mater. Sci. 22, 121-152 (1992).

Buffiere et al., Acta mater. vol. 47, No. 5, pp. 1613-1625, 1999.

* cited by examiner

HIGH-TEMPERATURE STRAIN CELL FOR TOMOGRAPHIC IMAGING

RELATED APPLICATIONS

This application claims priority to U.S. Provisional Patent Application No. 61/734,737, filed Dec. 7, 2012, which is herein incorporated by reference.

STATEMENT OF GOVERNMENT SUPPORT

This invention was made with government support under Contract No. DE-AC02-05CH11231 awarded by the U.S. Department of Energy and under Contract No. FA9550-09-1-0477 awarded by the Air Force Office of Scientific Research. The government has certain rights in this invention.

TECHNICAL FIELD

This disclosure is related to high temperature testing of materials, and more specifically to high-temperature strain cells for tomographic imaging.

BACKGROUND

Tomography generally refers to imaging by sections or sectioning, using any kind of penetrating wave. For example, X-ray computed micro-tomography (μ-CT), using the high fluxes from synchrotron sources, has evolved into a powerful imaging tool in the fields of physical and biological sciences due to its ability to image structure in three-dimensions (3-D) with high spatial resolution at macroscopic to sub-microscopic scales. With the development of increasingly complex structural materials that are finding increasing use in cutting-edge aerospace applications, such as fiber-reinforced ceramic composites and polymer-matrix composites, 3-D characterization of both structure and damage processes is essential, for it is the geometry, scale, and nature of these structures in all three dimensions that control their properties.

The last decade has witnessed the emergence of strong and tough ceramic-matrix composites, within which various design strategies are used on different spatial scales to overcome the brittleness that is inherent in materials that are able to survive extreme temperatures and chemically corrosive environments. Strong continuous fiber bundles (scale of 0.1 millimeters (mm) to 1 mm) are woven in custom-designed 3-D patterns, with individual bundles oriented in space so that they will follow the primary load paths expected in a given component to maximize its strength, and interlocked with one another to prevent catastrophic separation when damaged. Larger interstices between the fiber bundles may be partially filled with randomly-oriented fine reinforcing rods (scale of 1 micron (μm) to 10 μm), inhibiting local cracking under thermal shock. Coatings applied to individual fibers (scale of 0.1 μm to 1 μm) inhibit chemical reactions and ensure that the interfaces between the fibers and the matrix remain weak, allowing a ductile response through matrix cracking and frictional pullout of crack-bridging fibers. The remaining space between coated fibers, fiber bundles, and reinforcing rods is filled with a ceramic-matrix material, which itself may be a hybrid containing, for example, graphitic sheets that inhibit oxygen ingress (scale of 1 nanometer (nm) to 100 nm). Thus, like many natural materials, these new ceramic composites achieve robustness through complexity: their hierarchical, hybrid microstructure impedes the growth of local damage and prevents the large fatal cracks that are characteristic of brittle materials.

However, complexity in composition brings complexity in safe use. Most engineering structures, airframes, ships, buildings, etc., are designed to tolerate quite large cracks, which can be safely left monitored but unattended if they are less than a critical length, e.g., 10 mm or more in an airframe. Such cracks are large compared to the internal microstructural heterogeneity of a conventional material, which makes the prediction of their growth relatively easy; the effects of heterogeneity on crack growth tend to average out and therefore need not be included explicitly in engineering safety codes. For ceramic composites in ultrahigh-temperature applications, especially where corrosive species in the environment must be kept out of the material, relatively small cracks, on the order of the thickness of a fiber bundle (about 1 mm), can be unacceptable. These new ceramic materials thus violate the simplifying maxim of most traditional materials, that they be considered homogeneous on the scale at which damage becomes critical.

Exactly how micro-cracks are restrained by such tailored microstructure becomes the central question for the materials scientist who seeks to find the optimal composition or architecture and the design engineer who must predict the failure envelope. These questions raise many challenges, and the conditions of interest may be extreme. Observational methods based on direct imaging of the surface are complicated by high thermal noise. The properties (strength, etc.) of the composite's constituent materials and their interfaces are generally unknown at high temperature; they are also difficult to calibrate by independent tests, because the strength of different phases combined at nanometer and micron scales is not represented by tests on large specimens of the phase isolated as a monolithic material.

SUMMARY

An apparatus that allows for x-ray micro-tomography of a sample that is undergoing stress testing at up to about 2000° C. in a specific atmosphere and methods of using such an apparatus are described herein.

One innovative aspect of the subject matter described in this disclosure can be implemented an apparatus including a chamber, with the chamber comprising a top portion and a bottom portion. The top portion and the bottom portion are each joined to a window material, with the window material separating the top portion and the bottom portion and configured to transmit radiation used to characterize a sample. The top portion of the chamber defines a first port configured for a first cooled fixture. The bottom portion of the chamber defines a second port configured for a second cooled fixture. The first cooled fixture and the second cooled fixture are configured to hold the sample in the chamber. The top portion of the chamber and the bottom portion of the chamber further define a plurality of heating lamp ports. The plurality of heating lamp ports are configured for a plurality heating lamps, with the plurality of heating lamps positioned to heat the sample.

In some embodiments, the window material separates the top portion and the bottom portion of the chamber by up to about 2 centimeters.

Another innovative aspect of the subject matter described in this disclosure can be implemented a method including providing an apparatus. The apparatus may include a chamber. The chamber may comprise a top portion and a bottom portion, with the top portion and the bottom portion each joined to a window material, and the window material separating the top portion and the bottom portion and configured to transmit radiation used to characterize a sample. A first cooled fixture and a second cooled fixture may be mounted to the chamber and configured to hold the sample in the chamber. A plurality of heating lamps may be mounted to the chamber and positioned to heat the sample. The sample may be placed in the first and the second cooled fixtures. The sample may be heated to a specific temperature using the heating lamps. Radiation may be directed though the window material, the radiation thereafter interacting with the sample and exiting the chamber through the window material.

In some embodiments, a force is applied to the first cooled fixture that is transmitted to the sample.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

INTRODUCTION

Measurements made at high temperature are the only faithful source of the details of failure. If a test specimen is cooled to an experimentally convenient 25° C. for examination, the very act of cooling introduces thermal strains, on the order of at least 0.1% to 0.5% depending on composition and cooling rate, which can change the cracking patterns present before such cracks can be measured. In situ tomographic observations of deformation in an aluminum alloy have been made at temperatures as high as 555° C. However, this temperature is much lower than the range of interest for ceramic composites. Research to enable the mechanical and 3-D structural characterization of ceramic composites and other materials in situ, i.e., under load at high temperatures, is described herein.

APPARATUS

An apparatus that allows for real-time μ-CT under tensile or compressive loads at very high temperatures for the 3-D imaging of materials using synchrotron x-rays is described herein. Examples of schematic illustrations of an apparatus and its working principles are shown in FIGS. 1-3.

Figure 1:
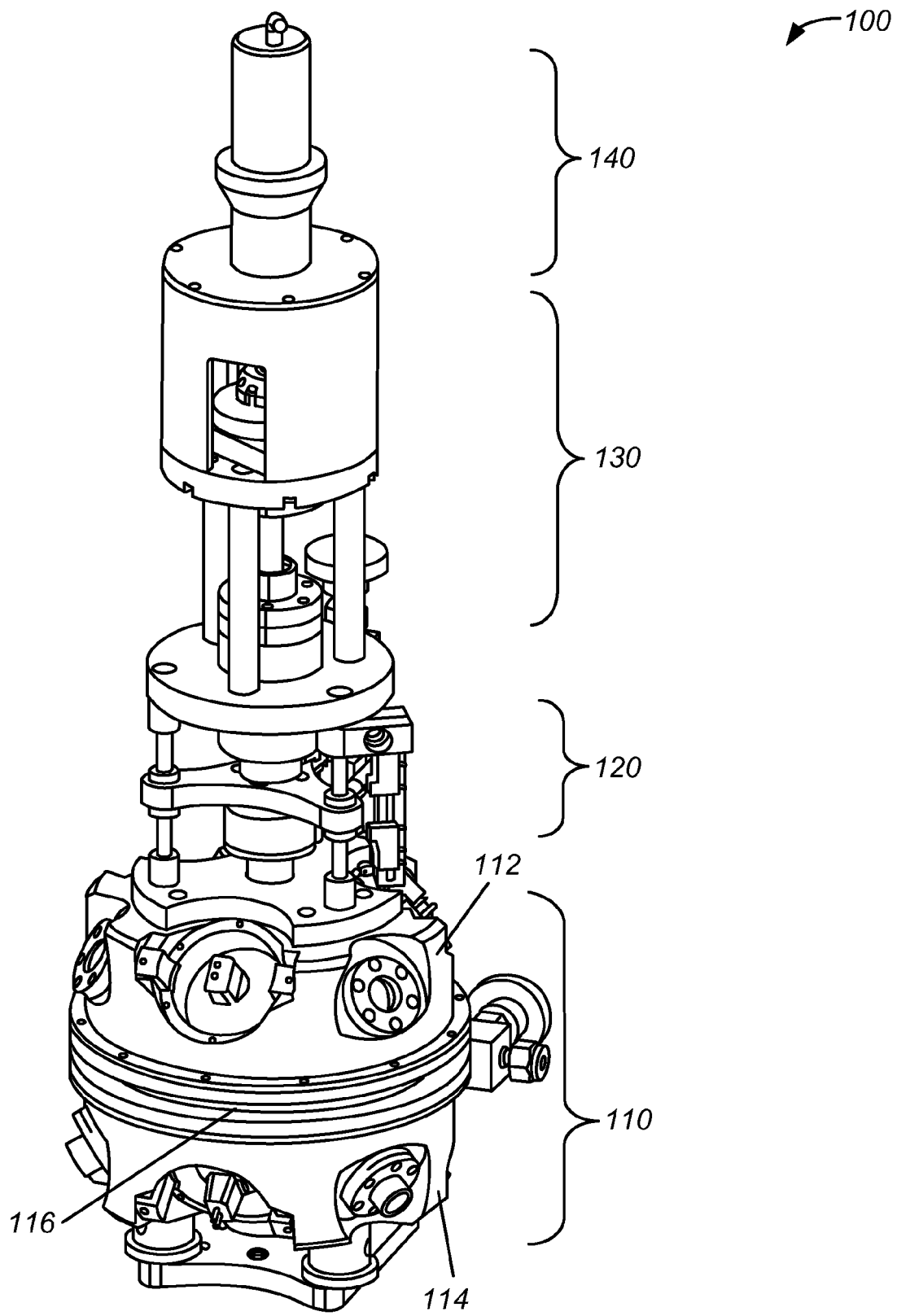
FIG. 1 shows an example of a schematic illustration of an in situ high-temperature test apparatus.

FIG. 1 shows an example of a schematic illustration of an in situ high-temperature test apparatus. As shown in FIG. 1, the in situ high-temperature test apparatus 100 includes a chamber 110, a load feedback module 120, a linear actuator stage 130, and a motor 140. The chamber 110 includes a top portion 112, a bottom portion 114, and a window material 116. In some embodiments, the top portion 112 and the bottom portion 114 are each joined or attached to the window material 116, with the window material 116 separating the top portion 112 and the bottom portion 114. In some embodiment, the window material is able to or configured to transmit radiation used to characterize a sample held in the chamber 110.

Figure 2:
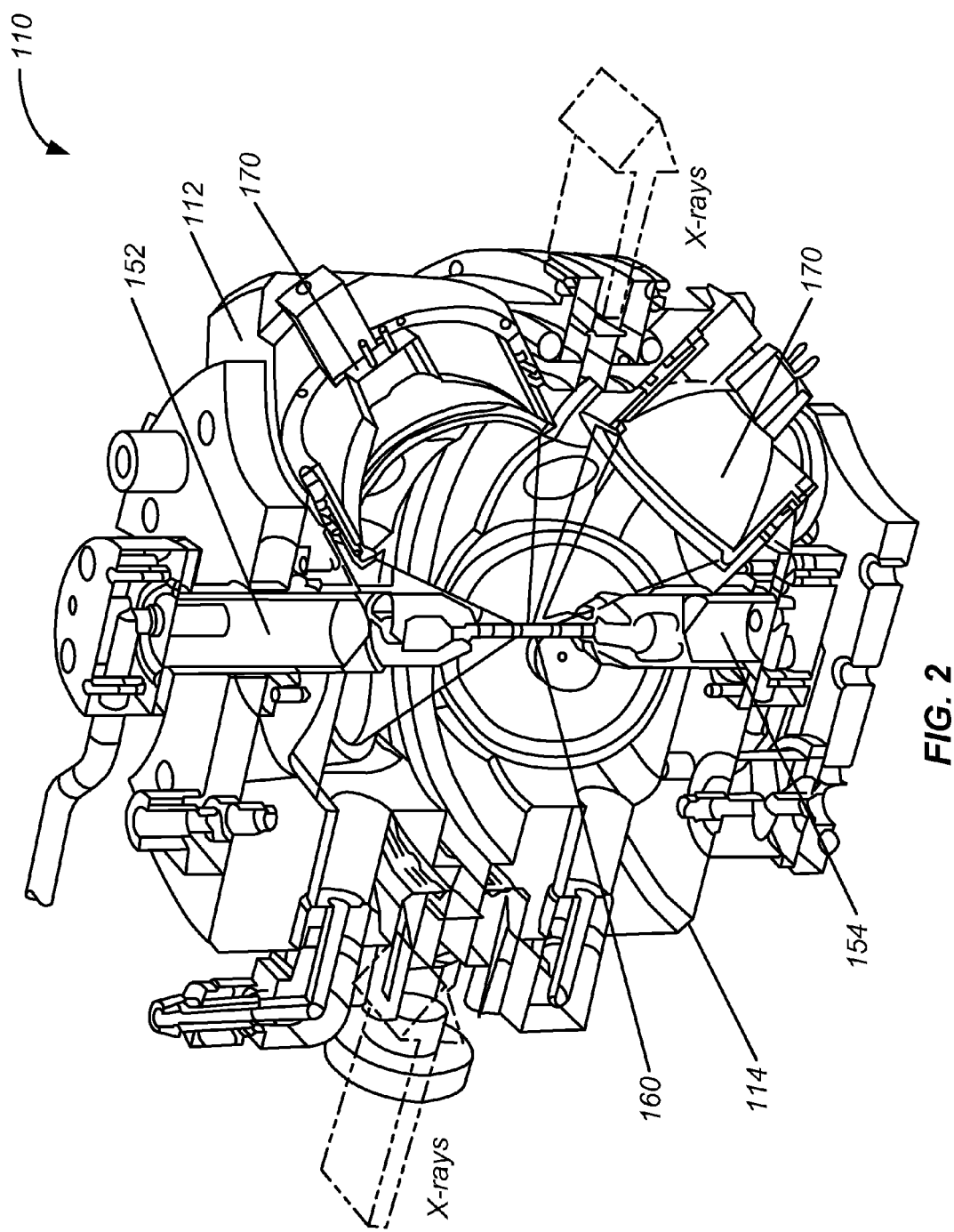
FIG. 2 shows an example of a schematic illustration of a chamber of an in situ high-temperature test apparatus.
Figure 3:
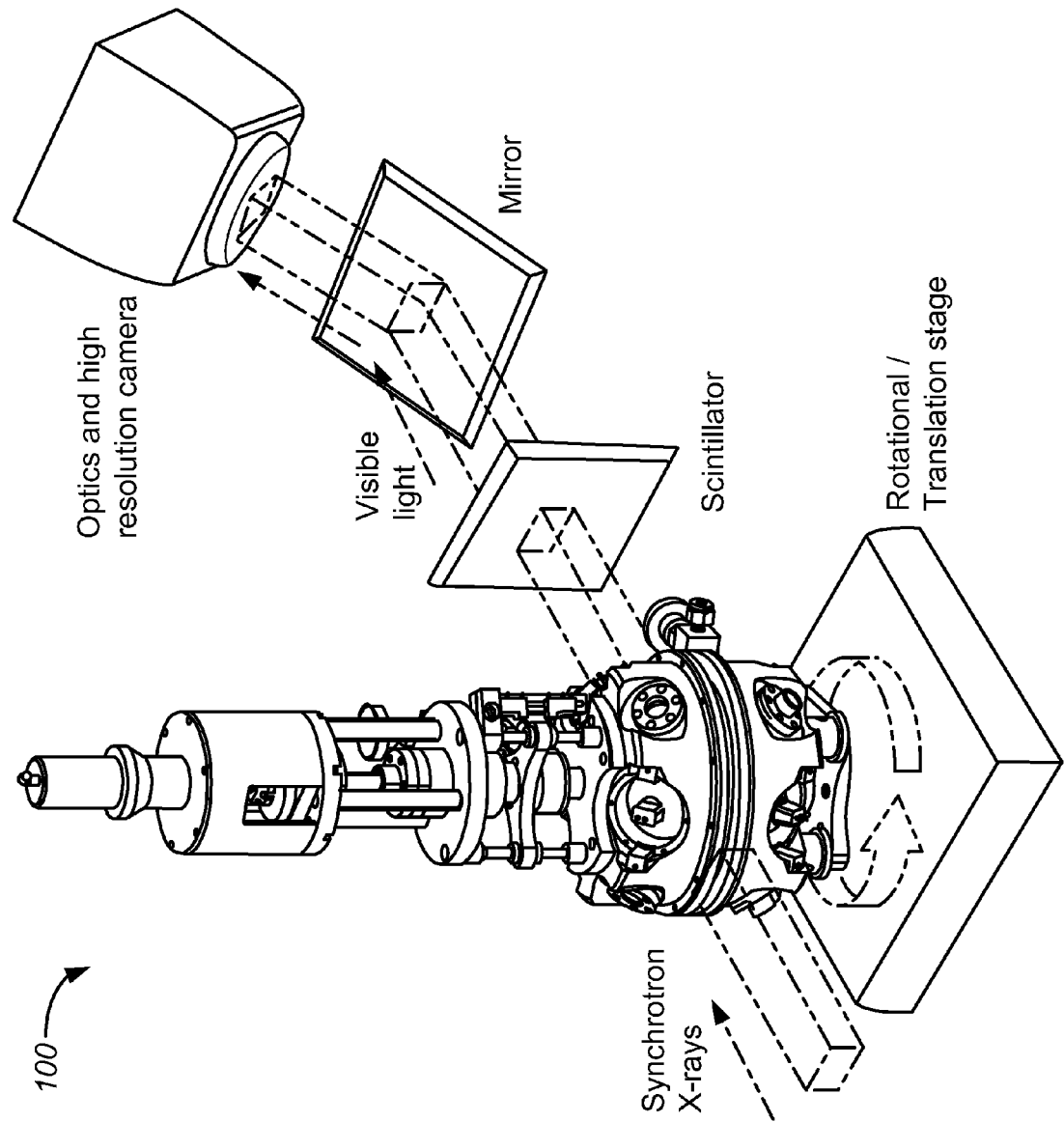
FIG. 3 shows an example of a schematic illustration of an in situ high-temperature test apparatus as used in an experiment.

FIG. 2 shows an example of a schematic illustration of the chamber 110 of the in situ high-temperature test apparatus 100. The top portion 112 of the chamber 110 defines a first port (not shown) configured for or to accept a first cooled fixture. The bottom portion 114 of the chamber 110 defines a second port (now shown) configured for or to accept a second cooled fixture. In some embodiments, the chamber 110 further includes a first cooled fixture 152 and a second cooled fixture 154. The first cooled fixture 152 and the second cooled fixture 154 may be mounted or attached to the chamber and configured to hold a sample 160 in the chamber.

The top portion 112 of the chamber and the bottom portion 114 of the chamber further define a plurality of heating lamp ports (not shown). The plurality of heating lamp ports are configured for or to accept a plurality heating lamps; that is, each of the plurality of heating lamp ports is configured for each of the plurality of heating lamps. The plurality of heating lamps ports are positioned so that the heating lamps can heat the sample 160. In some embodiments, the chamber 110 further includes the plurality of heating lamps 170.

In some embodiments, the chamber 110 is configured to hold or maintain a vacuum or a sub-atmospheric partial pressure. In some embodiments, the chamber 110 is configured to hold or maintain a pressure above atmospheric pressure. Depending on the sample to be measured, the atmosphere in the chamber may be specified. For example, a non-oxidizing atmosphere may be established by flowing an inert gas (e.g., ultra-high purity nitrogen) into the chamber 110 through an inlet port while a vacuum is maintained by continuously pumping the chamber. As another example, a high pressure steam atmosphere may be used to simulate, for example, gasses inside a turbine.

The shape of the chamber 110 may be specified such that the plurality of heating lamps 170 is able to be positioned to heat the sample 160. In some embodiments, each of the plurality of heating lamps 170 is focused so that a majority of the infrared (IR) light generated by each of the heating lamps is concentrated on the sample 160. Focusing each of the plurality of heating lamps 170 on the sample 160 may aid in preventing IR light from being distributed around the chamber 110 and heating various components in the chamber 110.

In some embodiments, the chamber 110 has a substantially spherical or a substantially cylindrical shape. For example, the top portion 112 and the bottom portion 114 of the chamber 110 may each have a substantially hemispherical shape. The window material 116 may be positioned at or near a great circle of the substantially spherical shape formed by the top portion 112 and the bottom portion 114 of the chamber 110. The sample 160 may be positioned at or near a center of the chamber 110. In this arrangement, a single plane includes the window material 116 and the sample 160. In some embodiments, the chamber 110 may define a volume having a substantially spherical shape.

As another example, the top portion 112 and the bottom portion 114 of the chamber 110 may each have a substantially cylindrical shape. The window material 116 may be positioned at a circumference of the substantially cylindrical shape formed by the top portion 112 and the bottom portion 114 of the chamber 110. The sample 160 may be positioned at or near a center of the circumference of the chamber 110, and at a height in the chamber 110 such that a single plane includes the window material 116 and the sample 160.

In some embodiments, the top portion 112 and the bottom portion 114 of the chamber comprise stainless steel or aluminum. Stainless steel may be used when the atmosphere in the chamber will be corrosive or otherwise demanding. For example, stainless steel may be used for top portion 112 and the bottom portion 114 of the chamber 110 when the atmosphere will be high pressure steam.

The window material 116 may be specified such that window material transmits the electromagnetic radiation that will be used to characterize the sample 160. In some embodiments, the window material 116 is selected from a group comprising aluminum, beryllium, pyrolytic carbon, and glassy carbon. In some embodiments, the window material is about 200 microns to 400 microns thick, or about 300 microns thick. In some embodiments, the window material 160 separates the top portion 112 and the bottom portion 114 of the chamber 110 by up to about 2 cm. In some embodiments, the window material 160 separates the top portion 112 and the bottom portion 114 of the chamber 110 by about 4 mm to 10 mm, or about 7 mm. In some embodiments, an epoxy-based glue (e.g., a thermosetting epoxy) is used to attach or bond the window material 116 to the top portion 112 and the bottom portion 114 of the chamber 110. For example, the epoxy-based glue may be a low-outgas sing glue, so as to aid in maintaining a specific atmosphere in the chamber 110 when the apparatus 100 is in operation.

In some embodiments, the window material 116 has a substantially cylindrical shape when separating the top portion 112 and the bottom portion 114 of the chamber 110. The window material 116 having a substantially cylindrical shape may allow radiation to enter one region of the window material, travel through the sample 160, and then exit another region of the window material. In some embodiments, the sample 160 is at a center of a circle defined by the substantially cylindrical shaped window material 116. In some embodiments, the window material 160 has an inner diameter of about 8 centimeters (cm) to 26 cm, or about 17 cm.

With the window material 116 separating the top portion 112 and the bottom portion 114 of the chamber 110, the window material supports the weight of the top portion 112 of the chamber. Further, when a force is applied to the first cooled fixture 154 and to the sample 160, there is an opposite force which is imparted to the chamber 110. As the chamber 110 includes the window material 116, the window material is also subjected to the force applied to the sample 160. The thickness of the window material 116 is a compromise between strength of the window material and radiation transmission characteristics of the window material; a thinner window material generally will transmit more radiation.

In some embodiments, the first and the second cooled fixtures 152 and 154 are configured to hold the sample 160 so that a compressive force or a tensile force may be applied to the sample. In some embodiments, the first and the second cooled fixtures 152 and 154 are water-cooled fixtures. In some embodiments, the first cooled fixture 152 includes a vacuum feed-through or other type of sealed feed-through associated with the interface of the first cooled fixture and the chamber 110 that allows for the transmission of a force to the sample 160. In some embodiments, the first and the second cooled fixtures 152 and 154 may include self-aligning ball and socket fixtures.

In some embodiments, the plurality of heating lamps 170 mounted to the chamber 110 comprises overhead projector lamps. In some embodiments, the plurality of heating lamps 170 comprises halogen lamps. For example, the heating lamps may be 150 watt halogen lamps. The plurality of heating lamps 170 may be symmetrically or uniformly positioned about the sample 160. For example, in some embodiments, the plurality of heating lamps 170 includes six heating lamps arranged in a hexapole arrangement. In some embodiments, each of the plurality of heating lamps 170 includes an ellipsoidal reflector positioned to focus radiation generated by the heating lamp onto a region of the sample 160. In some embodiments, the region of the sample 160 has dimensions of about 2.5 mm to 7.5 mm, or about 5 mm.

In some embodiments, the chamber 110 further comprises a plurality of seals or gaskets (not shown). In some embodiments, the seals or gaskets comprise O-rings (not shown). An O-ring is a mechanical gasket in the shape of a torus. O-rings generally comprise an elastomer with a round cross-section. Some O-rings are designed to be seated in a groove and compressed during assembly between two or more parts, creating a seal at the interface. A seal or gasket may be disposed between the top portion 112 or the bottom portion 114 of the chamber 110 and each of the plurality of heating lamps 170. Each of the plurality of seals or gaskets may be configured to create a seal between the chamber 110 and each of the plurality of heating lamps 170.

The temperature of the sample 160 may be controlled by regulating the voltage and the current applied to the plurality of heating lamps 170. In some embodiments, the apparatus 100 may further include a pyrometer (not shown) that is used to measure the temperature of the sample 160. In some embodiments, the apparatus 100 may further include a thermocouple (not shown) that is used to measure the temperature of the sample 160.

The motor 140 is positioned to apply a load or a force to the first cooled fixture 152. The load or force may be transmitted to the sample 160 held by the first and the second cooled fixtures 152 and 154. In some embodiments, the motor is a DC motor or servomotor. In some embodiments, the motor 140 is a stepper motor. In some embodiments, the motor 140 is a harmonic stepper motor. A harmonic stepper motor may allow a specific load or force to be applied to the sample. In some embodiments, the force applied to the sample is a compressive force. In some embodiments, the force applied to the sample is a tensile force. The linear actuator stage 130 may be disposed between the motor 140 and the chamber 110. The linear actuator stage 130 may include a gear box configured to translate output from the motor 140 to a liner displacement.

The load feedback module 120 also may be positioned between the motor 140 and the chamber 110. The load feedback module 120 may include a force measuring device (e.g., a load cell) and a displacement measuring device (e.g., a linear variable differential transformer (LVDT)). In some embodiments, the force measuring device is configured to measure the force applied to the sample 160 by the motor 140. In some embodiments, the displacement measuring device is configured to measure a displacement of the first cooled fixture 152 and the sample 160.

Apparatus described herein also may include a system controller (not shown) having instructions for controlling operations in accordance with the disclosed embodiments. The system controller will typically include one or more memory devices and one or more processors configured to execute the instructions so that the apparatus will perform a method in accordance with the disclosed embodiments. For example, a system controller may control the motor, record output from the force measuring device and the displacement measuring device, and control the temperature of the sample with a feedback loop including a temperature measurement of the sample and controlling the power input to the plurality of heating lamps. Machine-readable media containing instructions for controlling process operations in accordance with the disclosed embodiments may be coupled to the system controller.

FIG. 3 shows an example of a schematic illustration of the in situ high-temperature test apparatus 100 as used in an experiment. X-rays from a synchrotron may enter the window material of the apparatus 100, interact with a sample in the chamber, and then exit the window material. After exiting the window material of the apparatus 100, the x-rays may interact with imaging components (e.g., a scintillator to generate visible light and a mirror to reflect the visible light) and then imaged with optics and a high resolution camera.

While the apparatus 100 described above is described as using x-rays generated with a synchrotron, similar apparatus may be used with other x-ray sources and other radiation sources. Further, while the apparatus 100 described above is described as employing heating lamps, other heating sources may be used. For example, a sample may be heated using a resistive heating technique. As another example, a sample may be heated using lasers (e.g., multi-wavelength lasers). Lasers could be arranged similar to the manner in which the plurality of heating lamps is arranged, with the heating lamp ports of the chamber being covered with a material that allows for transmission of electromagnetic radiation from the laser.

An embodiment of an in situ high-temperature test apparatus was constructed and used for the experiments described below in the EXPERIMENTS section. Notable features of the constructed apparatus included the ability to maintain an in situ temperature environment of up to about 1750° C. in inert or oxidizing atmospheres with a controlled load applied to the sample, while simultaneously imaging the sample in real time with x-rays. The system (i.e., the apparatus, radiation source, and imaging devices) was capable of generating 3-D tomograms at a sufficiently high spatial resolution of less than about 1 μm/voxel (e.g., 0.65 μm/voxel) to image structural details at the micro-scale and to resolve the opening displacements of internal microcracks and other forms of internal damage as a function of load; a voxel is a volumetric pixel or Volumetric Picture Element.

The sample was held by water-cooled grips in the center of a vacuum-sealed cell of diameter about 170 mm, which could be evacuated and backfilled with a selected gas. Heating was provided by a hexapole arrangement of 150 watt halogen lamps, each with an ellipsoidal reflector aimed at the center of the cell, giving a spherical hot zone of diameter about 5 mm. Temperatures of test samples in the hot zone were determined from separate calibration of the heating lamp power with thermocouples. The waist of the cell consisted of a cylindrical aluminum window (300 microns thick, 7 mm height), which allowed x-rays to illuminate the sample and pass through to an x-ray imaging system comprising a scintillator coupled with microscope optics to a digital camera. For each scan, a set of 1200 radiographs can be collected and converted to a reconstructed 3-D tomographic image using inverse radon transforms.

Load was applied to the sample by a motor, while force and displacement were measured using an in-line load cell and a linear variable differential transformer (LVDT) sensor. The 360 degree aluminum thin x-ray window supported both the weight of the upper half of the test cell and the force applied to the sample during testing; thus its thickness was a compromise between strength and x-ray transmission. The thickness of 300 μm allows tensile forces up to 2 kN to be applied to the test sample while obtaining x-ray transmission of about 90% with the filtered white light (2.5 mm aluminum filter) used for sample illumination.

Images formed with the coherent synchrotron x-ray source contained a mixture of phase and absorption contrast, which emphasized edges and could make quantitative measurement of crack openings difficult. To minimize phase-contrast effects, the Modified Bronnikov Algorithm (MBA) and filtered back-projection can be used to obtain a 3-D tomographic reconstruction of the phase signal, enabling more accurate quantitative structural measurements.

METHOD

Figure 4:
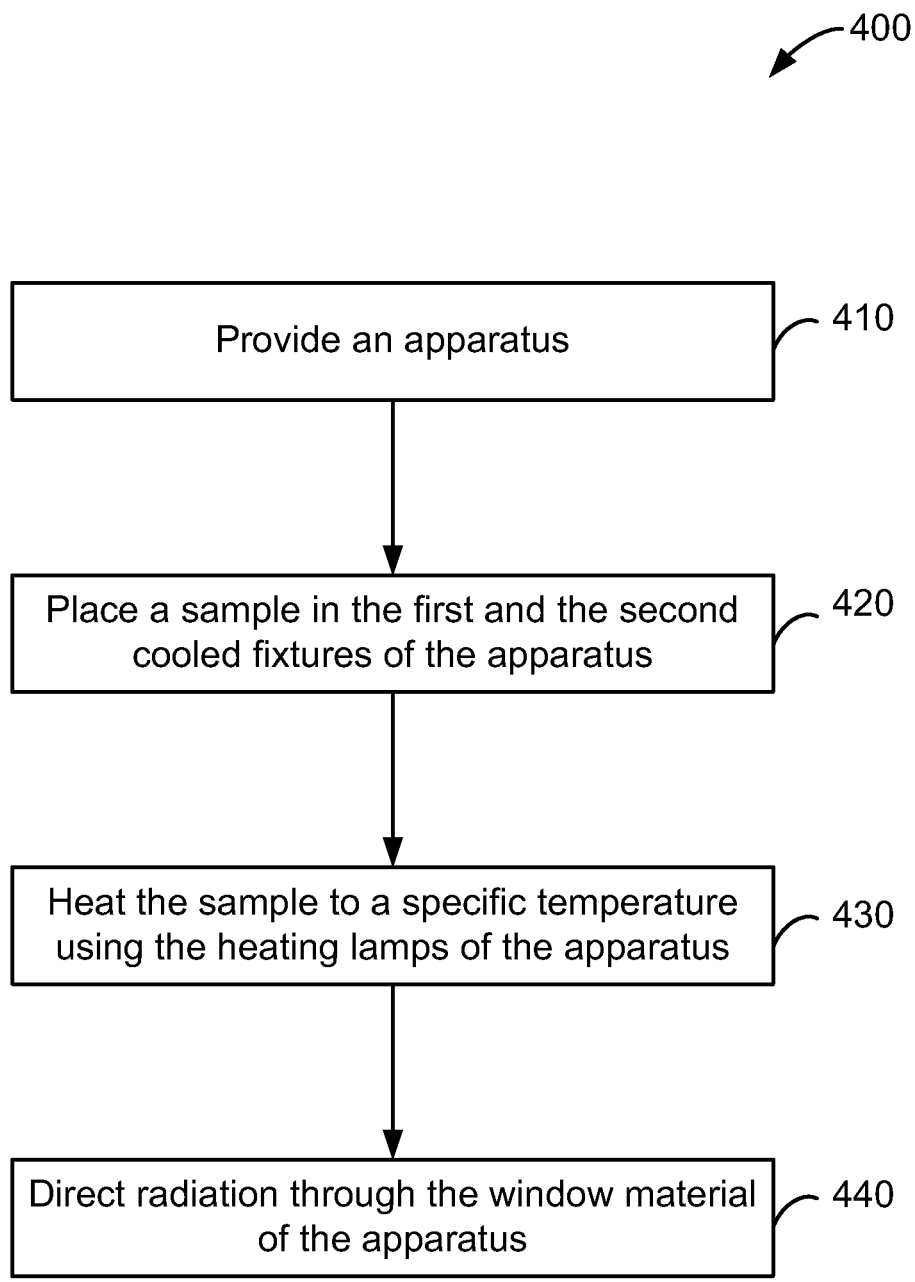
FIG. 4 shows an example of a process that may be performed with an in situ high-temperature test apparatus.

FIG. 4 shows an example of a process that may be performed with an in situ high-temperature test apparatus. In operation 410 of the method 400, an apparatus is provided. In some embodiments, the apparatus included a chamber, a first cooled fixture, a second cooled fixture, and a plurality of heating lamps. The chamber may comprise a top portion and a bottom portion, the top portion and the bottom portion each joined to a window material, with the window material separating the top portion and the bottom portion and configured to transmit radiation used to characterize a sample. The first cooled fixture and the second cooled fixture may be mounted to the chamber and configured to hold the sample in the chamber. The plurality of heating lamps also may be mounted to the chamber and positioned to heat the sample. For example, the apparatus may be the apparatus 100 described with respect to FIGS. 1-3.

In operation 420, a sample may be placed in the first and the second cooled fixtures of the apparatus. In operation 430, the sample may be heated to a specific temperature using the plurality of heating lamps. In some embodiments, the specific temperature is above about 1700° C. In some embodiments, the specific temperature is about 1750° C. In operation 440, radiation may be directed though the window material, the radiation thereafter interacting with the sample and exiting the chamber though the window material. In some embodiments, the radiation is radiation produced by a synchrotron source.

In some embodiments, the environment or atmosphere in the chamber during operations 430 and 440 can be controlled. For example, in some embodiments, the environment is a non-oxidizing environment. A non-oxidizing environment may be established and maintained by admitting a low flow of high purity nitrogen to the chamber while establishing a pressure of about $10^{-3}$ torr in the chamber. In some embodiments, the environment is an oxidizing environment.

In some embodiments, a force is applied to the first cooled fixture that is transmitted to the sample. In some embodiments, the force transmitted to the sample is a compressive force. In some embodiments, the force transmitted to the sample is a tensile force. In some embodiments, the force applied to the first cooled fixture about 2 kN or less. In some embodiments, the first and the second cooled fixtures are cooled with water.

EXPERIMENTS

The following description is intended to be an example of the embodiments disclosed herein, and is not intended to be limiting. Described below are the experimental setup and experiments performed with an embodiment of an in situ high-temperature test apparatus. The hard X-ray beamline BL 8.3.2 at the Advanced Light Source (Lawrence Berkeley National Laboratory, CA) was used for the µ-CT tomography experiments. The in situ high-temperature test apparatus was mounted on an air bearing rotation stage that was positioned in the beam by means of translations stages. The test apparatus was connected via multiple hoses and cables to ancillary units that support vacuum, chilled water circulation, inert gases, and electrical systems powering the heat lamps. These hoses and cables were carefully routed to ensure the required high stability and alignment of the rotation axis, which is important for generating high quality 3-D images. In the case of the high-temperature experiments, a non-oxidizing environment was maintained by admitting a low flow of high purity nitrogen while pumping to $10^{-3}$ torr.

Tomography data for each specimen were collected while tensile forces were applied in steps, increasing monotonically from 10 N until the peak load carrying capacity was exceeded. Each image consists of several tiled scans to increase the field of view.

The in situ high-temperature test apparatus allows imaging a maximum sample length of 7 mm, restricted by the height of the x-ray transmission window. The field of view in a given scan is a function of the magnification of the detection system and the size of the digital camera. For smaller, single tow specimens, a magnification corresponding to 0.65 µm m/voxel was used, giving a vertical field of view of approximately 1.4 mm. The full 3-D dataset for this sample consisted of four adjacent scans "tiled" along the vertical direction, covering over 5.5 mm of the sample; for textile composite specimens the data were collected in two vertical tiles with a magnification corresponding to 1.3 µm/voxel, covering nearly 5 mm total of the specimen. The total data sets for the single tow and textile composite specimens were roughly $16 \times 10^9$ and $8 \times 10^9$ voxels in size.

The micro-computed tomography (µ-CT) experiments were carried out in white light mode (polychromatic x-rays) with a sample-to-detector distance of 150 mm. Each scan consisted of multiple exposures, each of 100 ms, collected at 0.125° angular steps over a 180° rotation of the sample. Tomographic slices were generated using a commercial reconstruction algorithm. The whole dataset consisted of 2700 axial 16-bit grayscale slices each with a 0.65 µm isotropic voxel resolution for the single tow SiC specimen and a 1.3 µm isotropic voxel resolution for the beam sized textile composite specimens. Data were processed using image processing tools and visualized using visualization tools. For crack segmentation, the wavelet-FFT algorithm (referred to as xStripes) was adapted for use with the visualization tools. Transverse µ-CT slices parallel to the axis of the fibers produced striped patterns of the fibers which are eliminated by the wavelet-FFT filter. These filtered slices contain grayscale information of cracks alone, which were binarized and further segmented to obtain the crack opening measurements.

Measurement of high temperatures in the test setup was challenging as the small size of the test samples precluded directly attaching or embedding thermocouples. In the experiments, the sample temperatures in the hot zone were estimated from separate calibration tests, in which a C-type tungsten-rhenium thermocouple (maximum measureable temperature of 2300° C.) was mounted into the top grips and translated across the field of view using the motorized loading stage, with x-ray transmission images being used to determine the thermocouple position. The variation within the central 5 mm of the field of view was approximately 150° C. at the set temperature of 1750° C. The operating temperature range can be adjusted for a particular sample using calibrated voltage and current settings for the heating lamps.

There was some uncertainty in this temperature measurement approach because the temperature resulting from radiant heating is influenced by surface emissivity and thermal conductivity of the test sample. A system for in situ temperature measurement using a pyrometer is being developed. This requires rapid switching and spectral measurement to avoid errors due to reflection of light emitted by the visible-IR heat lamps. Preliminary measurements have indicated temperatures similar to those observed using the in situ thermocouple probe.

CONCLUSION

In situ x-ray micro-tomography for studying advanced materials that are being designed for future ultrahigh temperature environments has been demonstrated. A means to acquire real-time high-resolution (e.g., up to 0.65 µm/voxel) 3-D structural data for ceramic-matrix composites has been described, with the ability to observe microstructure and damage under load at different hierarchical length-scales (e.g., from a micrometer to several millimeters) at temperatures as high as 1750° C. The results include vital information pertaining to the underlying failure mechanisms within ceramic composites that can be used to optimize their performance.

Further details regarding the disclosed embodiments can be found in the manuscript Bale et al., "Real-time quantitative imaging of failure events in materials under load at temperatures above 1,600° C.," Nature Materials 12, 40-46 (2013), which is herein incorporated by reference.

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. An apparatus comprising:
   a chamber, the chamber comprising a top portion and a bottom portion, the top portion and the bottom portion each joined to a window material, the window material separating the top portion and the bottom portion and configured to transmit radiation used to characterize a sample, the top portion of the chamber defining a first port configured for a first cooled fixture, the bottom portion of the chamber defining a second port configured for a second cooled fixture, the first cooled fixture and the second cooled fixture configured to hold the sample in the chamber, the top portion of the chamber and the bottom portion of the chamber further defining a plurality of heating lamp ports, the plurality of heating lamp ports configured for a plurality heating lamps, the plurality of heating lamps positioned to heat the sample.

2. The apparatus of claim 1, wherein the chamber is configured to maintain a vacuum.

3. The apparatus of claim 1, wherein the window material is selected from a group consisting of aluminum, beryllium, pyrolytic carbon, and glassy carbon.

4. The apparatus of claim 1, wherein the window material is about 200 microns to 400 microns thick.

5. The apparatus of claim 1, wherein the window material has an inner diameter of about 8 centimeters to 26 centimeters.

6. The apparatus of claim 1, wherein the window material has a substantially cylindrical shape.

7. The apparatus of claim 1, wherein the window material separates the top portion and the bottom portion of the chamber by up to about 2 centimeters.

8. The apparatus of claim 1, wherein the chamber defines a volume having a substantially spherical shape.

9. The apparatus of claim 1, wherein the plurality of heating lamp ports comprises six heating lamps ports arranged in a hexapole arrangement.

10. The apparatus of claim 1, further comprising:
the plurality of heating lamps.

11. The apparatus of claim 10, wherein the plurality of heating lamps includes halogen lamps.

12. The apparatus of claim 10, further comprising:
a plurality of gaskets, a gasket disposed between the top portion or the bottom portion of the chamber and each of the plurality of heating lamps, each of the plurality of gaskets configured to create a seal between the chamber and each of the plurality of heating lamps.

13. The apparatus of claim 1, further comprising:
the first cooled fixture; and
the second cooled fixture.

14. The apparatus of claim 13, further comprising:
a motor positioned to apply a force to the first cooled fixture that is transmitted to the sample.

15. The apparatus of claim 14, further comprising:
a force measuring device positioned between the motor and the chamber, wherein the force measuring device is configured to measure the force applied to the sample by the motor.

16. The apparatus of claim 13, further comprising:
a displacement measuring device positioned between the motor and the chamber, wherein the displacement measuring device is configured to measure a displacement of the first cooled fixture.

17. A method comprising:
providing an apparatus, the apparatus including:
a chamber, the chamber comprising a top portion and a bottom portion, the top portion and the bottom portion each joined to a window material, the window material separating the top portion and the bottom portion and configured to transmit radiation used to characterize a sample;
a first cooled fixture and a second cooled fixture mounted to the chamber and configured to hold the sample in the chamber; and
a plurality of heating lamps mounted to the chamber and positioned to heat the sample;
placing the sample in the first and the second cooled fixtures;
heating the sample to a specific temperature using the heating lamps; and
directing the radiation though the window material, the radiation thereafter interacting with the sample and exiting the chamber through the window material.

18. The method of claim 17, further comprising:
applying a force to the first cooled fixture that is transmitted to the sample.

19. The apparatus of claim 18, wherein the force is a compressive force.

20. The apparatus of claim 18, wherein the force is a tensile force.

* * * * *